United States Patent
Munro et al.

(10) Patent No.: US 6,444,637 B1
(45) Date of Patent: Sep. 3, 2002

(54) REACTION OF ALKENES WITH EPOXIDES, THE PRODUCTS THEREOF AND THEIR USE AS FRAGRANCE COMPOUNDS

(75) Inventors: David Munro, Maidstone; Charles S. Sell, Aldington, both of (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/530,258

(22) PCT Filed: Oct. 21, 1998

(86) PCT No.: PCT/GB98/03139

§ 371 (c)(1),
(2), (4) Date: Jun. 22, 2000

(87) PCT Pub. No.: WO99/21817

PCT Pub. Date: May 6, 1999

(30) Foreign Application Priority Data

Oct. 28, 1997 (EP) ............................................. 97308582

(51) Int. Cl.$^7$ ................................................. A61K 7/46
(52) U.S. Cl. ..................... 512/12; 512/1; 512/8; 512/11; 512/25; 568/485; 568/667; 568/579; 568/821
(58) Field of Search ................................ 568/485, 667, 568/579, 821; 512/1, 8, 11, 25, 12

(56) References Cited

U.S. PATENT DOCUMENTS

| | | | |
|---|---|---|---|
| 3,845,078 A | * 10/1974 | Lemberg | ................... 568/667 |
| 4,853,368 A | * 8/1989 | Neinhaus et al. | ............. 512/25 |
| 4,948,780 A | 8/1990 | Hafner et al. | .................. 512/8 |
| 6,303,836 B1 | * 10/2001 | Ebel et al. | ................... 568/821 |

OTHER PUBLICATIONS

Fischli, "Cob(1)alamin als Katalysator 4. Mitteilung. Reduktion von alpha, betaungesattigten nitrilen", Helvetica Chimica Acta, vol. 62, No. 3, XP–002059981, 1979, pp. 882–893.

Zakharkin, et al., "Synthesis of 13–oxabicyclo(10.3.0)pentadecane from cyclododecanone", Journal of Organic Chemistry of the USSR, vol. 26, No. 9, Part 2, XP002059982, Sep. 1990, pp. 1696–1699.

Zalharkin, et al., "Synthesis of 1–ethynylcododecanol and its isomerization at a vanadium catalyst", Journal of Organic Chemistry of the USSR, vol. 25, No. 4, Part 2, XP–002059983, 1989, pp. 699–701.

* cited by examiner

Primary Examiner—Jill Warden
Assistant Examiner—Monique T. Cole
(74) Attorney, Agent, or Firm—Morgan, Lewis & Bockius LLP

(57) ABSTRACT

Lewis acid-catalyzed reaction of an alkene, including cycloalkenes, with an epoxide to provide an aldehyde which may be reduced to the corresponding alcohol. The reaction products may be used to provide perfumes or perfume products.

14 Claims, 9 Drawing Sheets

REACTION OF ALKENES WITH EPOXIDES, THE PRODUCTS THEREOF AND THEIR USE AS FRAGRANCE COMPOUNDS

FIELD OF THE INVENTION

The present invention concerns reaction of alkenes, including cycloalkenes. In this specification, references to alkenes should be construed as covering alkenes and cycloalkenes where appropriate.

SUMMARY OF THE INVENTION

In one aspect the present invention provides the Lewis acid-catalysed reaction of an alkene with an epoxide. This is a novel reaction, useful for synthesis of various fragrance materials (known and novel) and their intermediates.

One of the main products of reaction is an alkanal (or aldehyde), and the reaction of the invention appears to be generally applicable to the synthesis of homologous aldehyde from open-chain alkenes. The resulting aldehyde may then be subjected to further reaction, such as reduction to the corresponding alkanol (or alcohol).

In a further aspect, the present invention thus provides a method of synthesis of an aldehyde by Lewis acid-catalysed reaction of an alkene with an epoxide.

For example, reaction of cyclododecene and propylene oxide produces 2-(cyclododecyl) propan-1-al. This alkanal can be readily reduced to the corresponding alkanol, 2-(cyclododecyl)propan-1-ol, e.g. by catalytic reduction using sodium borohydride. 2-(cyclododecyl)propan-1-of is a known compound which exhibits an intense and tenacious odour of amber character, and so is useful in fragrance compositions and in perfumed products, and is normally made from cyclododecanone in a more complex, costly and hazardous synthesis. The present invention thus provides an alternative route to production of the useful fragrance material 2-(cyclododecyl)propan-1-ol.

In a preferred aspect, the invention thus provides a method of producing 2-(cyclododecyl) propan-1-ol, comprising treating cyclododecene with propylene oxide in the presence of a Lewis acid catalyst to produce 2-(cyclododecyl)propan-1-al, and reducing the 2-(cyclododecyl)propan-1-al to 2-(cyclododecyl)propan-1-ol.

A major by-product of the first step of this reaction is 2-methylperhydrocyclododeca[b]furan, which is also a known fragrance compound exhibiting a woody-amber odour, and which is marketed by Wacker under the trade name 'Lignoxan'. 'Lignoxan' is also normally made from cyclododecanone by a multistage procedure.

The present invention thus provides a novel route to produce two known useful fragrance materials, 2-(cyclododecyl)propan-1-ol and 2-methylperhydrocyclododeca[b]furan, by Lewis-acid catalysed-reaction of cyclododecene with epoxide.

The use of $SnCl_4$ as the Lewis acid is thought to be beneficial.

As a further example, reaction of 1,5,9-cyclododecatriene and propylene oxide produces 2-(cyclododecadienyl)-1-propanal. This material can be reduced, e.g. with sodium borohydride, to the corresponding alcohol, 2-(cyclododecadienyl)-1-propanol, which is a novel compound which exhibits an odour of amber and is the subject of our co-pending European patent application No. 97308580.6. Catalytic hydrogenation of 2-(cyclododecadienyl)-1-propanol yields 2-(cyclododecyl) propan-1-ol.

A minor product of the reaction of 1,5,9-cyclododecatriene and propylene oxide is 2-methyl-2,3,3a,4,5,8,9,12,13,13a-decahydrocyclododeca[b]furan, which can be hydrogenated to give 'Lignoxan'.

Minor components of the reaction of 1,5,9-cyclododecatriene with propylene oxide have been found to exhibit an intense blackcurrant odour that has been attributed to the novel compound 2-methylperhydro-as-indacenol [3a,3-b]furan that is the subject of our co-pending European patent application No. 9730851.4.

The present invention also includes within its scope products (direct and indirect) of reactions in accordance with the invention. Those reaction products having fragrance properties may be used as such to impart, strengthen or improve the odour of a wide variety of products, or they may be used as a component of a perfume to contribute its odour character to the overall odour of such perfume. For the purposes of this invention a perfume is intended to mean a mixture of fragrance materials, if desired mixed with or dissolved in a suitable solvent or mixed with a solid substrate, which is used to impart a desired odour to the skin and/or any product for which an agreeable odour is indispensable or desirable. Examples of such perfumed products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders, body deodorants and antiperspirants, etc.

Other fragrance materials which can be advantageously combined with the reaction products according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, keta's, nitrites, etc., including saturated and unsaturated compounds, aliphatic, carbocyclic and heterocyclic compounds.

Such fragrance materials are mentioned, for example, in S. Arctander, "Perfume and Flavor Chemicals" (Montclair, N.J., 1969), in S. Arctander, "Perfume and Flavor Materials of Natural Origin" (Elizabeth, N.J., 1960) and in "Flavor and Fragrance Materials—1991", Allured Publishing Co. Wheaton, Ill. USA.

Examples of fragrance materials which can be used in combination with the reaction products according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl) propanal, 3-(p-tert-butylphenyl)-propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2- pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate.

Solvents which can be used for perfumes which contain products according to the invention are, for example: ethanol, isopropanol, diethyleneglycol monoethyl ether, dipropylene glycol, diethyl phthalate, triethyl citrate, isopropyl myristate, etc.

The quantities in which reaction products according to the invention can be used in perfumes or in products to be perfumed may vary within wide limits and depend, inter alia, on the nature of the product, on the nature and the quantity of the other components of the perfume in which the compound is used and on the olfactive effect desired. It is therefore only possible to specify wide limits, which, however, provide sufficient information for the specialist in the art to be able to use reaction products according to the invention for his specific purpose. In perfumes an amount of 0.01% by weight or more of the reaction product according to the invention has been found to have a clearly perceptible olfactive effect. Preferably the amount is 0.1 to 80% by weight, more preferably at least 1%. The amount of the reaction product according to the invention present in products will frequently be at least 10 ppm by weight, preferably at least 100 ppm, more preferably at least 1000 ppm. However, levels of up to about 20% by weight may be used in particular cases, depending on the reaction product and the product to be perfumed.

The present invention thus also includes within its scope perfumes and perfumed products incorporating products of reactions in accordance with the invention.

The invention will be further described, by way of illustration in the following Examples and with reference to the accompanying figures, in which.

EXAMPLE 1

The AlCl$_3$-Catalysed Reaction of Cyclododecene with Propylene Oxide

Figure 1:
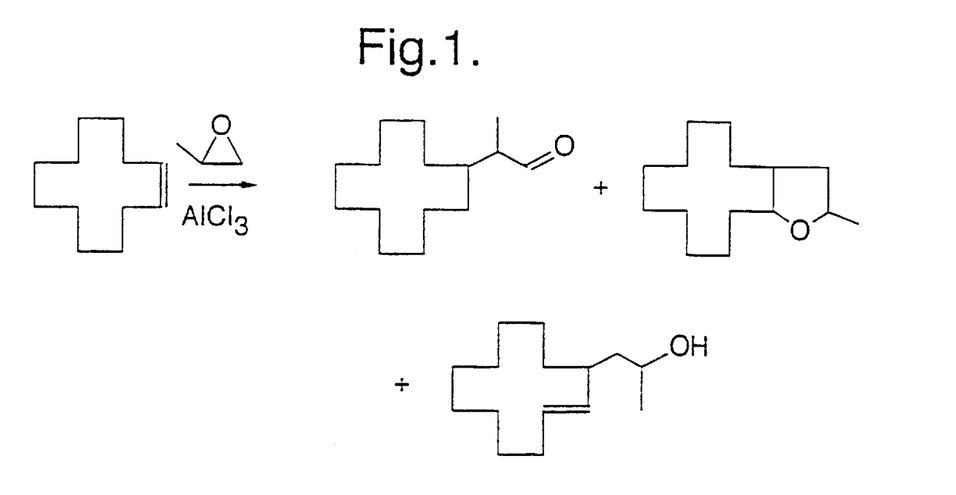
FIG. 1 is a reaction scheme for AlCl$_3$-catalysed reaction of cyclododecene with propylene oxide.

The AlCl$_3$-catalysed reaction of cyclododecene with propylene oxide at −30° C. in dichloromethane was found to give three major products, as shown in FIG. 1, which were not as anticipated.

The products were the aldehyde 2-(cyclododecyl)propan-1-at (referred to herein as QRM 2173), obtained directly in 25–30% yield, a fused furan, 2-methylperhydrocyclododeca[b]furan (referred to herein as QRM 2429), isolated in 18–20% yield, and a mixture of unsaturated alcohols, containing mainly 1-(2-cyclododecyl) propan-2-ol (referred to herein as QRM 2829), which could be isolated pure in a yield of 24–30%. The furan QRM 2429 is the same as a woody amber fragrance material sold by Wacker under the trade name Lignoxan, for which the reported route of production involves synthesis from cyclododecanone in a three step procedure.

Figure 2:
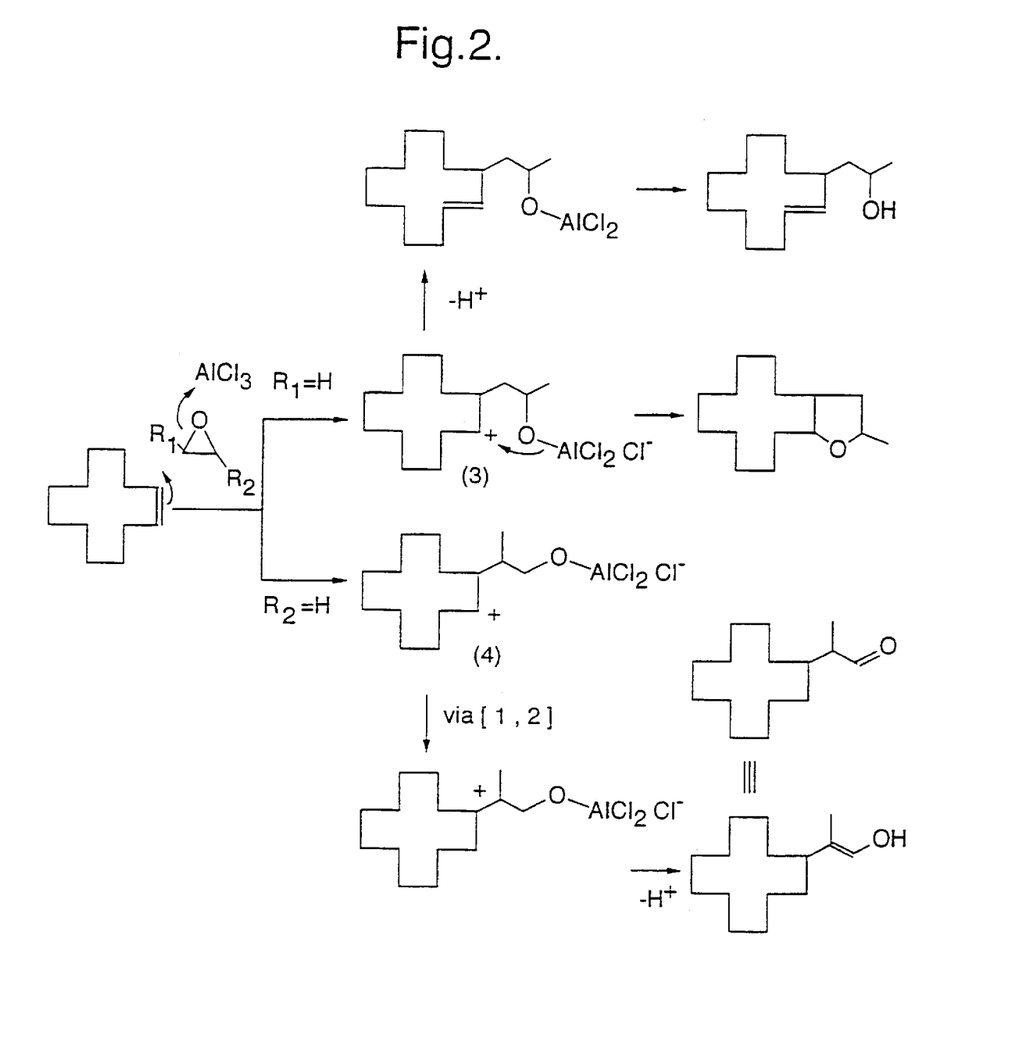
FIG. 2 illustrates further the reaction of FIG. 1.

In the present reaction, as illustrated in FIG. 2, it appears that two isomeric carbonium ion intermediates (3) and (4) are initially formed. Intermediate (3) can ring close to give the fused tetrahydrofuran system, QRM 2429, or can lose a proton to give the unsaturated alcohol QRM 2829. Intermediate (4) undergoes rearrangement by hydrogen shift to give the aldehyde QRM 2173.

Therefore, the Lewis acid-catalysed reaction of cyclododecene with propylene oxide is interesting in that it gives two useful products in a single step. Lignoxan (QRM 2429) is a fragrance material in its own right. The aldehyde 2-(cyclododecyl)propan-1-al (QRM 2173) has an ozone, seabreeze-like odour and can be readily reduced to the corresponding alcohol, 2-(cyclododecyl)propan-1-ol (referred to herein as QRM 2172) using inexpensive reagents. This alcohol is a known compound exhibiting an odour of amber character.

Finally, although the unsaturated alcohol QRM 2829 has no useful odour, it may be oxidised or alkylated to give materials of fragrance interest.

Reaction Protocol for the Synthesis of 2-(cyclododecyl) propan-1-ol from Cyclododecene a) Lewis Acid-Catalysed Reaction of Cyciododecene with Propylene Oxide Aluminium chloride (180 g; 1.35 mol) was suspended in CH$_2$Cl$_2$ (1 litre), and cooled to −30° C. A mixture of cyclododecene (200 g; 1.2 mol) and propylene oxide (100 g; 1.72 mol) was added dropwise with stirring under nitrogen, maintaining this temperature with external cooling. After complete addition (1 hour), the reaction mixture was immediately quenched into ice (2 litres) and diethyl ether (2 litres) was added. The organic layer was separated, washed and dried over magnesium sulphate.

Chromatography [silica] hexanel gave recovered cyclododecene (19.6 g). Further elution, using [hexane 90%; diethyl ether 10%] as eluent gave a colourless oil, identified as 2-(cyclododecyl) propan-1-al (QRM 2173) (61.3 g; 25.2%). Continued elution gave a colourless oil (44.6 g; 18.3%), identified as 2-methylperhydrocyclododeca[b]furan (QRM 2429—Lignoxan). Spectral characteristics of this material were identical to those of a commercial sample of Lignoxan (Wacker).

The solvent polarity was increased to [hexane 50%; diethyl ether 50%]. Following elution of two poorly-defined multicomponent mixtures (2.3 g+8.7 g), a further discrete major product was isolated as a colourless oil. This material was identified as E- and Z-1-(2-cyclododecenyl)propan-2-ol, (64.8 g; 26.6%). A sample (1 g) was short-path distilled, bp 140° C. at 1 mbar, M+224.

glc[SE54; 100–250° C. at 4° C./min] 22.645 min (11.3%), 22.976 min (72.0%).

| $^1$H NMR (CDCl$_3$) | Signal | Multiplicity | Area | Assignment |
|---|---|---|---|---|
| | 5.40 | d of t | 1 | H-3 cyclododecadiene |
| | 5.22 | d of d | 1 | H-2 cyclododecadiene |
| | 3.82 | m | 1 | C$\underline{H}$(CH$_3$)OH |
| | 2.40 | bs | 1 | OH |
| | 2.22–1.08 | m | 21 | CH$_2$ + C$\underline{H}$CH$_2$CH(CH$_3$)OH |
| | 1.13 | d | 3 | CH$_3$ |

$^{13}$C NMR (CDCl$_3$) 135.712($\underline{C}$H=CH), 132.229(CH=$\underline{C}$H), 67.690(CH(CH$_3$)OH), 45.964($\underline{C}$H$_2$CH(CH$_3$)OH), 41.866($\underline{C}$HCH$_2$CH(CH$_3$)OH, 34.049(CH$_2$), 32.449(CH$_2$), 26.524(CH$_2$), 26.131(CH$_2$), 26.094(CH$_2$), 25.728(CH$_2$), 24.677(CH$_2$), 23.625(CH$_2$), 23.552(CH$_2$), 23.415(CH$_2$), 22.775(CH$_3$).

b) Reduction of 2-(Cyclododecyl)propan-1-al (QRM 2173) to 2-(Cyclododecyl) propan-1-ol, (QRM 2172)

2-(Cyclododecyl)propan-1-al (60 g; 0.27 mol) obtained as described above was dissolved in ethanol (100 ml) and added dropwise to a stirred suspension of sodium borohydride (10 g; 0.26 mol) in ethanol (400 ml). After complete addition, most ethanol was removed in vacuo and a 50/50 mixture of dichloromethane/water was added. The reaction mixture was then stirred while adding 2N HCl (aq) dropwise until effervescence ceased. The organic layer was separated, washed and dried. TLC [silica, diethyl ether 50% hexane 50%] indicated a small amount of QRM 2429 contaminant from the aldehyde, then a very much more polar product.

Chromatography (as TLC) gave a colourless oil (1.2 g), identified as the furan QRM 2429, followed by a colourless oil (46.9 g). This material was vacuum distilled to give a colourless oil (39.1 g; 64.5%).

glc [SE 54: 100–250° C. at 4° C./min] 25.118 min (98.1%).

| $^1$H NMR (CDCl$_3$) | Signal | Multiplicity | Area | Assignment |
|---|---|---|---|---|
| | 3.52 | AB | 2 | C$\underline{H}_2$OH |
| | 1.88 | s | 1 | OH |
| | 1.68 | m | 1 | CH$_3$C$\underline{H}$ |
| | 1.55 | d of t | 1 | C$\underline{H}$CHCH$_3$ |
| | 1.50–1.23 | m | 22 | ring CH$_2$ |
| | 0.90 | d | 3 | CH$_3$ |

$^{13}$C NMR (CDCl$_3$) 66.867(CH$_2$OH), 38.054(CH), 34.406 (CH), 26.643(CH$_2$), 26.240(CH$_2$), 24.585(CH$_2$), 24.494 (CH$_2$), 24.466(CH$_2$), 24.357(CH$_2$), 23.561(CH$_2$), 23.543 (CH$_2$), 23.506(CH$_2$), 23.022(CH$_2$), 22.638(CH$_2$), 13.588 (CH$_3$).

EXAMPLE 2

Lewis Acid-Catalysed Reaction of 1,5,9-Cyclododecatriene with Propylene Oxide

Figure 3:
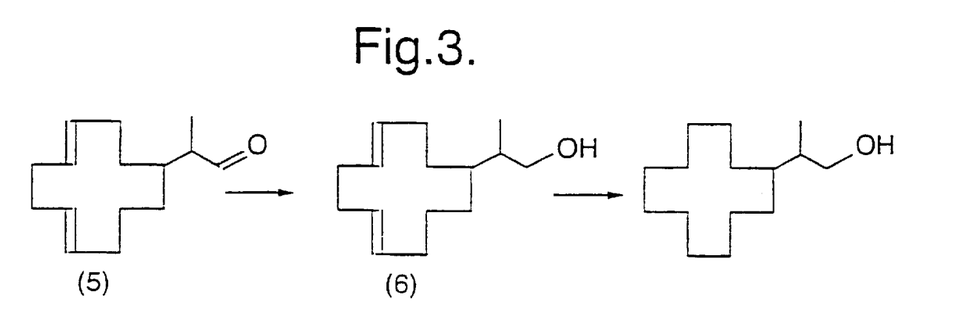
FIG. 3 is a reaction scheme for conversion of 2-(4,8-cyclododecadienyl)propan-1-al to 2-(4,8-cyclododecadienyl)propan-1-ol and 2-(cyclododecyl)propan-1-ol.

An alternative approach to synthesis of QRM 2172 would be to utilise a cheaper starting material in place of cyclododecene. In this respect, 1,5,9-cyclododecatriene is worthy of investigation. As shown in FIG. 3. the desired reaction product, 2-(4.8-cyclododecadienyl)propan-1-al (5) (referred to herein as QRM 2669) could be hydrogenated to give QRM 2172. It could also be reduced to give 2-(4,8-cyclododecadienyl)propan-1-ol (6) (referred to herein as QRM 2671), a novel molecule, which would have a strong possibility of exhibiting amber properties, together with improved biodegradability.

Figure 4:
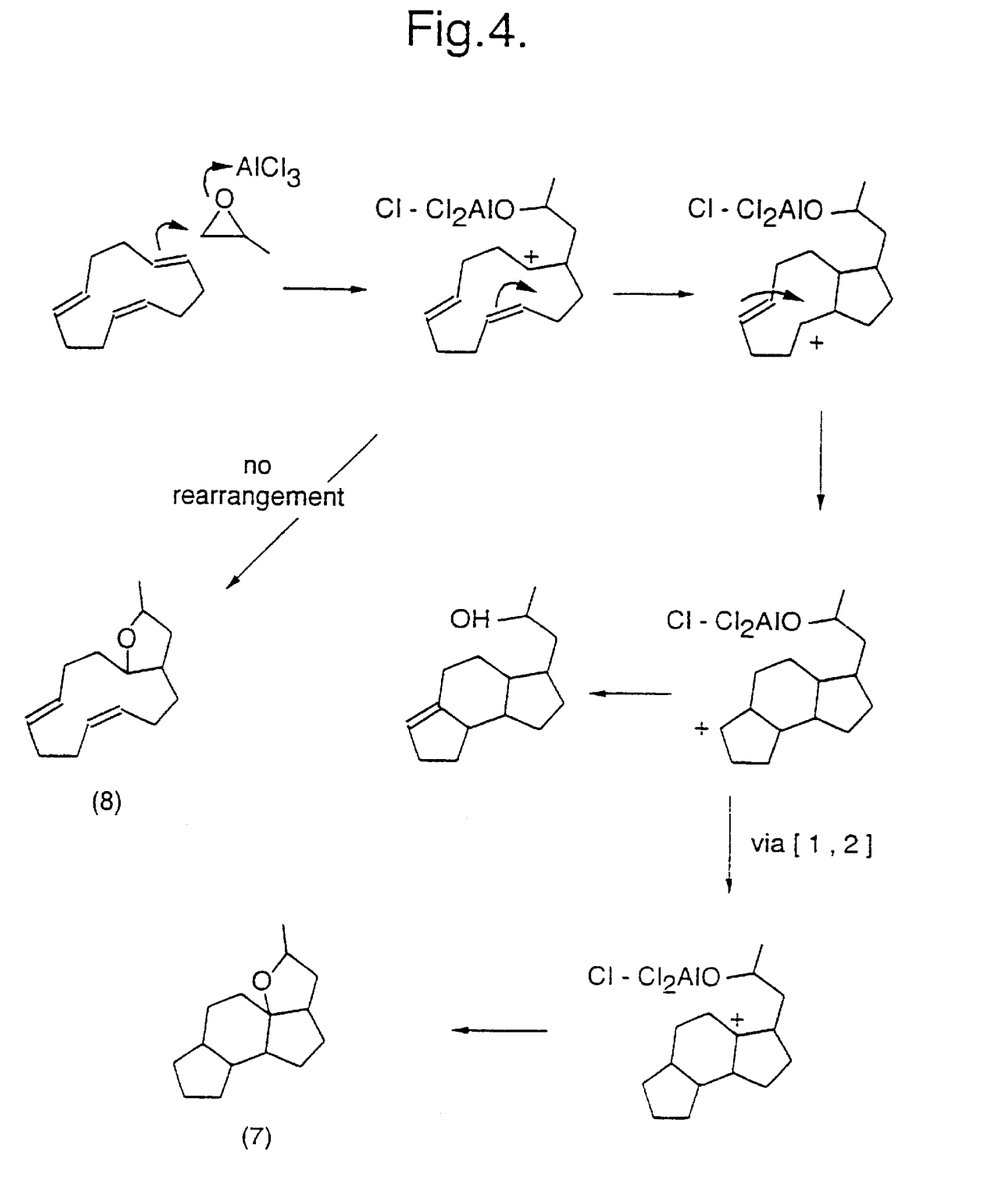
FIG. 4 illustrates the possibilities of double bond rearrangement and internal ring closure of 1,5,9-cyclododecatriene following formation of the carbonium ion.

However, when 1,5,9-cyclododecatriene is used as substrate in Lewis acid-catalysed reaction with propylene oxide, the reaction is complicated by the possibilities of double bond rearrangement and of internal ring closure following formation of the initial carbonium ion illustrated for attack to give the propan-2-ol side chain, as shown in FIG. 4.

Figure 5:
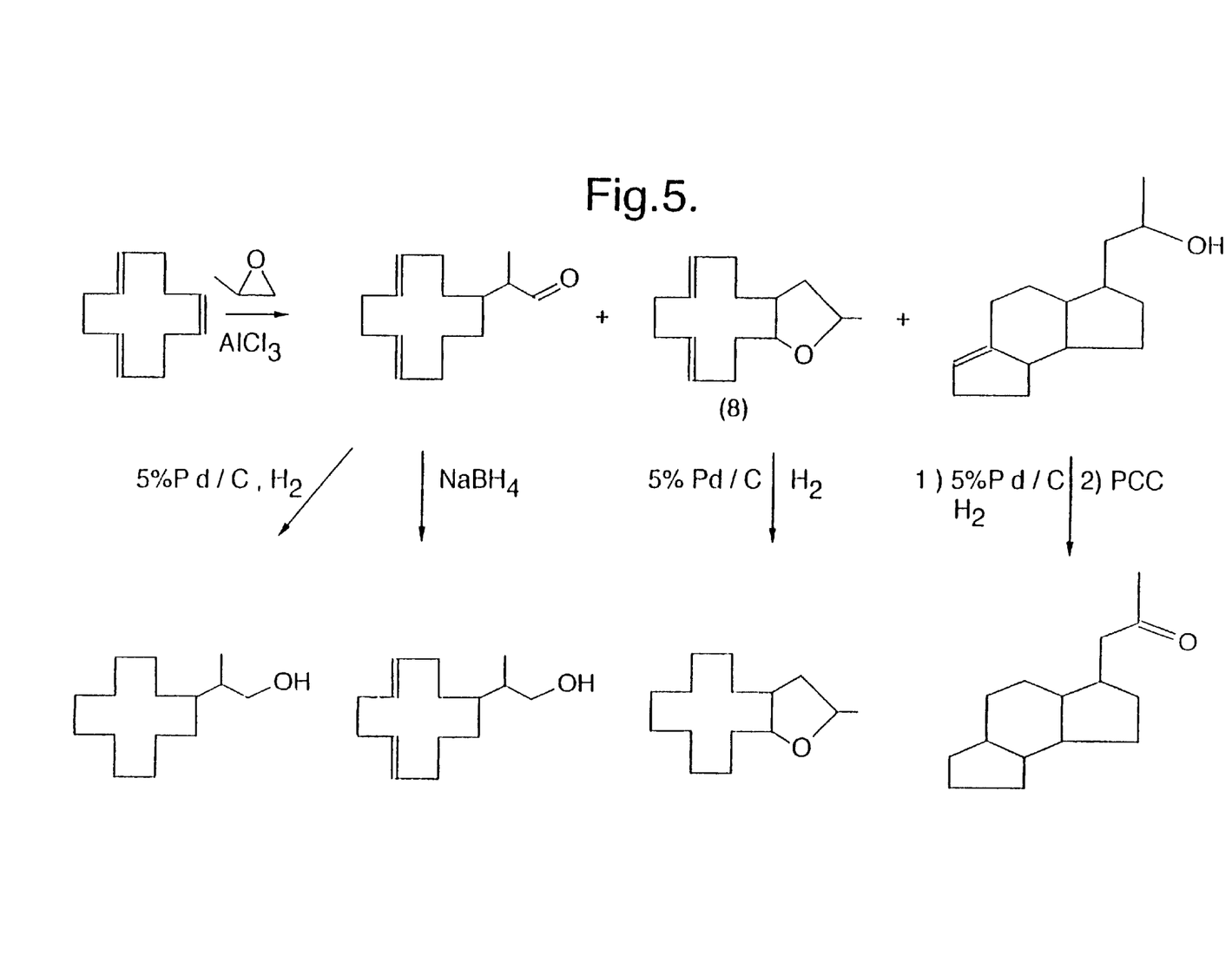
FIG. 5 is a reaction scheme for AlCl$_3$-catalysed reaction of 1,5,9-cyciododecatriene with propylene oxide, also showing products of further reaction.

When this reaction was investigated, three main products were obtained. as shown in FIG. 5. These products were the desired aldehyde, QRM 2669 (15–22% conversion, based on recovered cyclododecatriene), 2-methyl-2,3,3a,4,5,8,9,12, 13,13a-decahydro-cyclododeca[b]furan (8) which is an unsaturated analogue of QRM 2429 (5% conversion), and a complex mixture of isomeric (M+220) and higher molecular weight alcohols (40–55% conversion), from which the tricyclic propan-2-ol (referred to herein as QRM 2672) was isolated.

The structures of QRM 2669 and the furan (8) were confirmed by hydrogenation to give QRM 2172 (a known amber material obtainable from Wacker) and QRM 2429 (Lignoxan, Wacker), respectively, Sodium borohydride reduction of QRM 2669 gave 2-(cyclododecadienyl)propan-1-ol (QRM 2671) which is a novel amber material. Also of interest was the intense blackcurrant odour exhibited by the furan fraction. This was subsequently subjected to glc trapping and the minor component responsible for this odour was identified by $^{13}$C. NMR as 2-methylperhydro-as-indaceno[3a,3-b]furan (referred to herein as QRM 2670). This tetracyclic furan (which is shown at (7) in FIG. 4) is formed in low yield (isolated, here, in <0.1% yield) by a cascade reaction following formation of the initial carbonium ion as shown in FIG. 4. Reducing the reaction temperature to −70° C. gives an increased yield of product (7), but the yield remains only 1.6% (by glc), and extensive chromatographic purification is necessary to give 0.5% isolated yield.

Reaction Protocol for the Synthesis of QRM 2172 from 1,5,9-Cyclododecatriene a) Lewis Acid-Catalysed Reaction of 1,5,9-Cyclododecatriene with Propylene Oxide 1,5,9-Cyclododecatriene (150 g; 0.924 mol) and propylene oxide (69 g; 12 mol) were mixed together, and added, with stirring, to a suspension of AlCl$_3$ (129 g; 0.96 mol) in CH$_2$Cl$_2$ (750 ml) at −50° C. The reaction mixture was allowed to reach ambient temperature, then added to a mixture of ice (4000 ml) and diethyl ether (2000 ml). The ether layer was separated and dried over MgSO$_4$. Chromatography (silica; hexane) gave recovered 1,5,9-cyclododecatriene (51.2 g). Further elution, using a mixture of hexane (90%) and diethyl ether (10%) as eluent gave a pale yellow oil (27.2 g), which was identified as 2-(cyclododecadienyl)propan-1-al, (QRM 2669). M+220. Kovats 1755, 1773, 1775, 1781.

| $^1$H NMR (CDCl$_3$) | Signal | Multiplicity | Area | Assignment |
|---|---|---|---|---|
| | 9.78 | d | 1 | CHO |
| | 9.71 | d | | |
| | 5.60–5.12 | m | 4 | CH=CH |
| | 2.53–1.12 | m | 16 | CH$_2$ and CH |
| | 1.10 | d | 3 | CH$_3$ |
| | 0.94 | d | | |

Elution was continued, giving a small amount of a pale yellow oil (5.1 g). This was re-chromatographed, giving a fore-run (1.1 g) with an intense blackcurrant odour. The material was extremely complex, being a mixture of at least 15 components present at >1%.

glc{SE54; 100–250° C. at 4° C./min} 18.692 min (6.3%), 8.938 min (6.7%), 19.287 min (1.6%), 19.809 min (12.9%), 19.986 min (18.7%), 20.159 min (1.0%), 20.430 min (7.0%), 20.647 min (7.7%), 20.914 min (9.4%), 21.035 min (5.9%), 21.118 min (6.2%), 21.202 min (4.8%), 21.320 min (3.2%), 21.395 min (1.1%), 21.499 min (2.4%).

The most intense cassis odour was associated with the peaks at 19.809 min and 19.986 min. These were isolated by capillary glc trapping, using a modified HP5890 glc instrument, fitted with an HP5 column [SE 54 type], length 30 m, internal diameter 0.53 mm, surface coating 1.05 micrometre. The carrier gas was nitrogen, flow rate 2 ml mine$^{-1}$. The temperature programme utilised was 50° C. (0.5 min)/50° C. min$^{-1}$ to 100° C. at 10° C. min$^{-1}$ to 280° C. In excess of 400 cycles were used, giving a mixture of the two desired products, and allowing the identification of the major product as 2-methylperhydro-as-indaceno[3a,3-b]furan(QRM 2670).

$^{13}$C NMR (CDCl$_3$) Major isomer: 89.74 (quaternary, ether), 72.89(CH, ether), 50.33(CH), 43.57(CH), 40.44(CH), 39.32(CH$_2$), 38.99(CH$_2$), 37.02(CH), 32.81(CH$_2$), 32.58(CH$_2$), 30.88(CH$_2$), 29.73(CH$_2$), 29.61(CH$_2$), 23.34(CH$_3$), 21.75(CH$_2$).

Minor isomer: 93.39(quaternary ether), 72.84(CH, ether), 48.81(CH), 48.11(CH), 41.00(CH$_2$), 39.16(CH), 35.33(CH$_2$), 32.05(CH), 31.33(CH$_2$), 30.92(CH$_2$), 28.09(CH$_2$), 26.24(CH$_2$), 24.56(CH$_2$), 24.11(CH$_2$), 21.13(CH$_3$).

Further elution of the medium-pressure chromatography column gave a colourless oil (3.2 g), now having only a woody odour. This was identified as 2-methyl-2,3,3a,4,5,8,9,12,13,13a-decahydrocyclododeca[b]furan. M+220.

glc[SE54; 100–250° C. at 4° C./min] indicated 4 major isomers, 20.877 min (37.4%), 21.037 min (23.2%), 21.149 min (17.1%), 21.356 min (3.3%).

| $^1$H NMR (CDCl$_3$) | Signal | Multiplicity | Area | Assignment |
|---|---|---|---|---|
| | 5.52–5.08 | m | 4 | CH=CH |
| | 4.06 | overlapping d of t | 1 | CHOCHCH$_3$ |
| | 3.86 | d of q | | |
| | 3.74 | d of q | 1 | CHOCHCH$_3$ |
| | 2.31–0.83 | m | 15 | CH$_2$ + CH$_2$CHCH$_2$CHCH$_3$ |
| | 1.23 | overlapping d | 3 | CH$_3$ |

Finally, the solvent polarity of the original column was increased to a mixture of hexane (50%) and diethyl ether (50%). Further elution now gave a pale yellow oil (40.0 g), whose composition was more complex than either of the above isolated and identified products. $^1$H NMR indicated the presence of only one double bond, and of a propan-2-ol side chain. In order to attempt a structure elucidation, the sample was firstly distilled, giving two major products:

a) colourless oil (8.9 g), bp 131° C. at 3 mbar [alcohol #1]
b) colourless oil (1.3 g), bp 155° C. at 3 mbar [alcohol #2]

The remainder of the material was lost to a polymeric residue.

Alcohol #1 was subjected to catalytic hydrogenation, in order to remove the problem of double bond isomers. The material (8.2 g) was dissolved in ethanol (100 ml), and 5% Pd/C (1 g) was added. The reaction mixture was hydrogenated in a Buchi autoclave at 5 bar hydrogen pressure for 4 hours. The catalyst was then removed by filtration through Celite, and the solvent removed to give a colourless oil. This material was chromatographed to give a colourless oil (4.8 g). A sample (1.8 g) was short-path distilled, bp 140° C. at 3 mbar. M+222, confirming original presence of only one double bond.

| $^1$H NMR (CDCl$_3$) | Signal | Multiplicity | Area | Assignment |
|---|---|---|---|---|
| | 3.78 | m | 1 | CH$_2$CH(CH$_3$)OH |
| | 2.01 | s | 1 | OH |
| | 1.95–0.86 | m | 21 | ring + side chain CH$_2$ |
| | 1.21 | d | 3 | CH$_3$ |

The side chain of this material was subjected to oxidation, in order to obtain material of possible odour interest, and to obtain further spectral details on the ring system. A sample (3 g) of the above alcohol was, therefore, dissolved in CH$_2$Cl$_2$ (50 ml), and added dropwise to a stirred suspension of pyridinium chlorochromate (6 g) in CH$_2$Cl$_2$. After 1 hour, dietnyl ether (300 ml) was added, and the reaction mixture was filtered through Florisil. Chromatography [silica; hexane 90%, diethyl ether] gave a colourless oil (2.4 g), which was short-path distilled, bp 120° C. at 3 mbar. M+220. This material was assigned as 1-perhydro-as-indacen-3-yl-2-propanone (referred to herein as QRM 2747) and is shown in FIG. 5. This material has a woody, estery odour.

| $^1$H NMR (CDCl$_3$) | Signal | Multiplicity | Area | Assignment |
|---|---|---|---|---|
| | 2.42 | d | 2 | CH$_2$ propanone |
| | 2.05 | s | 3 | CH$_3$ propanone |
| | 2.63–0.84 | m | 19 | CH and CH$_2$ ring |

$^{13}$C NMR (CDCl$_3$) 208.555(C=O), 50.051(CH$_2$ propanone), 46.833(CH), 39.995(CH), 34.013(CH$_2$), 33.976

(CH), 31.919(CH), 31.370(CH), 30.465(CH$_3$), 30.181(CH), 28.755(CH$_2$), 28.700(CH$_2$), 28.353(CH$_2$), 26.469(CH$_2$), 21.952(CH$_2$).

Figure 6:
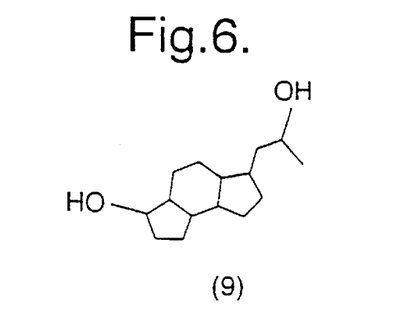
FIG. 6 shows the structure of 6-(2-hydroxypropyl) perhydro-as-indacen-3-ol.

Alcohol #2 was identified as 6-(2-hydroxypropyl) perhydro-as-indacen-3-ol, the structure of which is shown in FIG. 6. M+238.

This structure provides further evidence for the cascade reaction sequence shown in FIG. 4.

| $^1$H NMR (CDCl$_3$) | Signal | Multiplicity | Area | Assignment |
|---|---|---|---|---|
| | 4.30 | m | 1 | CHOH |
| | 3.85 | d of t | 1 | CHOH |
| | 2.41–0.95 | m | 19 | CH$_2$ + CH |
| | 1.14 | d | 3 | CH$_3$ |

$^{13}$C NMR (CDCl$_3$) 67.652(CHOH), 62.057(CHOH), 48.451(CH), 46.416(CH), 45.379(CH), 45.049(CH$_2$), 33.162(CH), 33.135(CH$_2$), 33.107(CH$_2$), 32.815(CH), 27.859(CH$_2$), 26.853(CH$_2$), 26.716(CH$_2$), 24.201(CH$_3$), 22.895(CH$_2$).

b) Reduction of 2-(Cyclododecadienyl)propan-1-al (QRM 2669) to give 2-(Cyclododecyl)-propan-1-ol (QRM 2172)

2-(Cyclododecadienyl)propan-1-al, (2.5 g), obtained as above, was dissolved in ethanol (100 ml), and 5% Pd/C added. The reaction mixture was hydrogenated in a Buchi autoclave at 5 bar hydrogen pressure for 6 hours. The catalyst was removed by filtration through Celite and the solvent removed to give a colourless oil (2.3 g). This material was identical in all respects ($^1$H and $^{13}$C NMR, M+, glc) to 2-(cyclododecyl)propan-1-ol prepared by either Wittig-Horner synthesis or by reaction of cyclododecene with propylene oxide, followed by reduction.

Reduction of 2-(Cyclododecadienyl)propan-1-al (QRM 2669) to 2-(cyclododecadienyl)propan-1-ol (QRM 2671)

2-(Cyclododecadienyi)propan-1-al (4 g; 0.018 mol), dissolved in ethanol (10 ml), was added dropwise to a suspension of NaBH$_4$ (1.0 g; 0.026 mol) in ethanol (80 ml). After complete addition, the reaction mixture was allowed to stir for 1 hour, then most ethanol was removed in vacuo. CH$_2$Cl$_2$ (150 ml) was then added, and the reaction mixture stirred while adding 2N HCl (aq) dropwise, until effervescence ceased. The organic layer was separated, washed and dried over MgSO$_4$. Chromatography (silica; hexane 50%, diethyl ether 50%) gave a colourless oil (3.3 g, 81%), identified as 2-(cyclododecadienyl)propan-1-ol. A sample (2 g) was short-path distilled, bp 115° C. at 1 mbar M+222. The material consists of five isomers.

| Kovats | Area |
|---|---|
| 1822 | 21.2% |
| 1836 | 14.0% |
| 1839 | 9.4% |
| 1845 | 22.5% |
| 1854 | 29.1% |
| Total: | 96.2% |

| $^1$H NMR (CDCl$_3$) | Signal | Multiplicity | Area | Assignment |
|---|---|---|---|---|
| | 5.50–5.08 | m | 4 | CH=CH |
| | 3.71–3.29 | AB complex | 2 | CH$_2$OH |
| | 2.20 | s | 1 | OH |
| | 2.38–1.02 | m | 16 | ring CH$_2$ + CHCH(CH$_3$)OH |
| | 1.00–0.79 | t overlapping | 3 | CH$_3$ |

$^{13}$C NMR (CDCl$_3$) 132.603, 132.567, 132.384, 132.311, 132.238, 132.064, 131.972, 131.680, 131.657, 131.570, 131.524, 131.360, 131.214, 129.650, 129.558, 129.357, 129.101, 128.955, 128.726, 128.397 (all CH=CH) 67.407, 65.803, 65.201, 64.003, 63.900 (all CH$_2$OH) 37.268, 36.317, 36.107, 35.220, 34.781 (all CH) 32.504, 31.608, 31.297, 30.858, 30.739, 29.313, 28.581,27.914, 27.146, 26.213, 25.317, 24.594, 23.781, 22.638 (all CH$_2$) 15.990, 15.505, 14.966 (CH) 10.952, 10.549 (CH$_3$)

EXAMPLE 3

The Lewis Acid-Catalysed Reaction of Epoxides with Cycloalkenes

Contrary to the well-known Friedel-Crafts reaction of aromatics, the use of alkenes as substrates is known to have problems as a reliable synthetic method, and the formation of reactive intermediates, which can undergo elimination or isomerisation, often results in complex mixtures. As far as we are aware, the Lewis Acid-catalysed reaction of epoxides with (cyclo)alkenes has not previously been proposed and so is novel.

All experiments were carried out in an identical manner, using the same molar ratios, method, and apparatus. The apparatus used was a 500 ml 3-necked RB reaction flask, equipped with an overhead stirrer, thermometer, pressure-equalised dropping flask, and condenser. The reaction was carried out under a nitrogen atmosphere. When SnCl$_4$, TiCl$_4$ and BCl$_3$ were used as the catalysts, these were introduced via syringe.

Firstly, dichloromethane (50 ml) was placed in the reaction flask, and the Lewis Acid (0.067 mol) was added. The mixture was then cooled to −15° C. in a CO$_2$/acetone bath, and stirred while adding a mixture of the cycloalkene (0.06 mol) and the epoxide (0.06 mol), over 10 minutes. The resulting reaction mixture was stirred for an hour at this temperature, then poured into ice (400 ml) and diethyl ether (250 ml) added. The organic layer was separated and dried over MgSO$_4$. This solution was analysed by glc [SE54; 100–250° C. at 4° C./min], then the solvent was removed in vacuo and the residue purified, initially by low pressure chromatography [silica; 10% diethyl ether, 90% hexane].

1) Effect of Lewis Acid

The effect of the Lewis acid on the reaction of cyclododecene with propylene oxide was investigated using various different Lewis acid catalysts, and not just AlCl$_3$ as used in Example 1.

Figure 7:
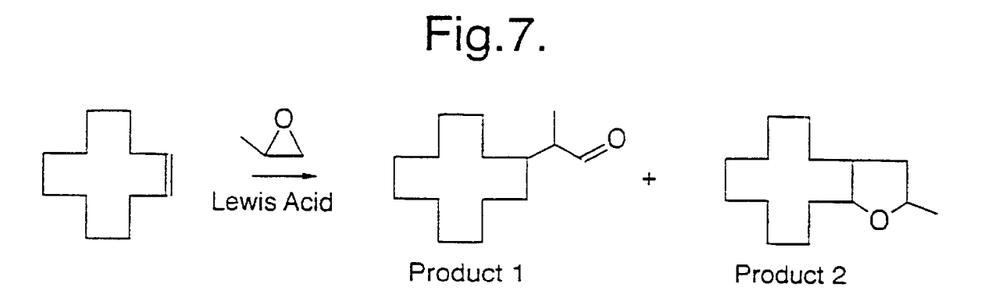
FIG. 7 is a reaction scheme for Lewis acid-catalysed reaction of cyclododecene with propylene oxide.

The general reaction is illustrated in FIG. 1. The amount of aldehyde (Product 1) and furan (Product 2) (FIG. 7) were analysed by glc, and the reaction mixture then worked up. The results, based on relative peak areas, are shown in Table 1.

TABLE 1

| Lewis Acid | Composition % Cyclododecene | Composition % Product 1 | Composition % Product 2 | % Conversion Product 1 | % Conversion Product 2 |
|---|---|---|---|---|---|
| $AlCl_3$ | 32.92 | 27.31 | 21.34 | 40.70 | 31.80 |
| $SnCl_2$ | 95.89 | 0 | 0 | 0 | 0 |
| $SnCl_4$ | 50.58 | 36.35 | 0.93 | 73.60 | 1.90 |
| $TiCl_4$ | 66.69 | 8.10 | 1.11 | 24.30 | 3.30 |
| $ZnCl_2$ | 93.43 | 0.05 | 0 | 0 | 0.80 |
| $BCl_3$ | 89.92 | 1.48 | 0.75 | 14.70 | 7.40 |

The most significant result from Table 1, above, is the encouragingly high conversion to the aldehyde, Product 1, where $SnCl_4$ is used as the catalyst. This could have a markedly beneficial effect on the economics of producing QRM 2172 by this route.

However, when 1,5,9-cyclododecatriene was utilised as the substrate, the use of $SnCl_4$, as catalyst did not translate into such a high conversion, probably due to the larger number of reaction manifolds open to the initial carbonium ion in this case. The reaction was, nonetheless, notable for being much cleaner and with less polymer formation than where $AlCl_3$, was the catalyst. The overall yield of 2-cyclododecadienyl-1-propanal was 17.3%.

2) Effect of Ring Size

Figure 8:
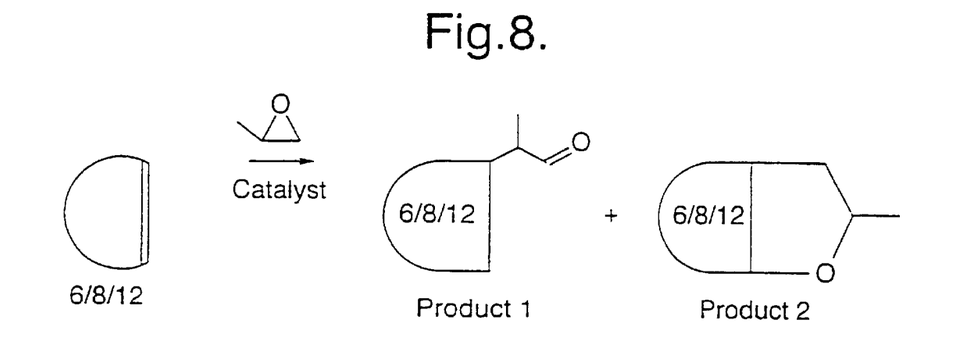
FIG. 8 shows the reaction of cycloalkenes of different ring sizes with propylene oxide, catalysed by the Lewis acid AlCl$_3$.

Cycloalkenes of three different ring sizes, namely cyclohexene, cyclooctene, and cyclododecene, were reacted with propylene oxide, catalysed by $AlCl_3$, as the Lewis acid, to investigate their effect on the reactivity of the respective rings, and whether this would affect the distribution of the products. The general reaction is illustrated in FIG. 8.

The results of glc relative peak area analysis are summarised in Table 2.

Figure 9:
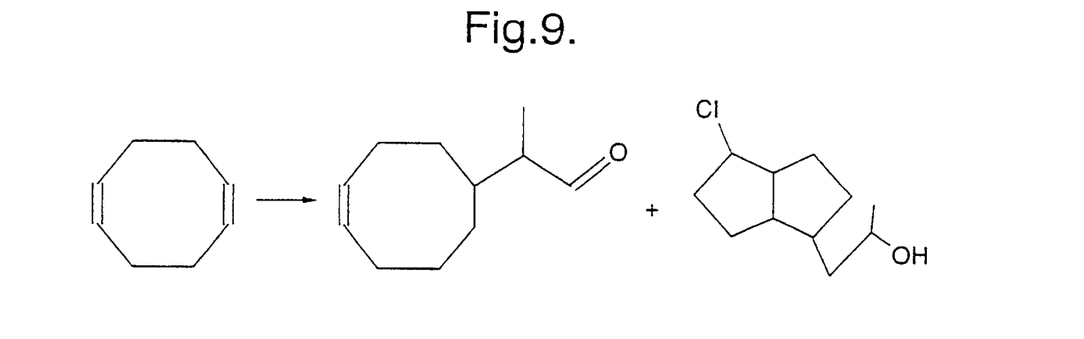
FIG. 9 is a reaction scheme for Lewis acid-catalysed reaction of 1,5-cyclooctadiene with propylene oxide.

When 1,5-cyclooctadiene was used as substrate, two major products were obtained. These were 2-(4-cyclooctenyl)propanal (referred to herein as QRM 2962), and 1-(4-chloroperhydro-1-pentalenyl)-2-propanol (referred to herein as QRM 2963), as shown in FIG. 9.

Figure 10:
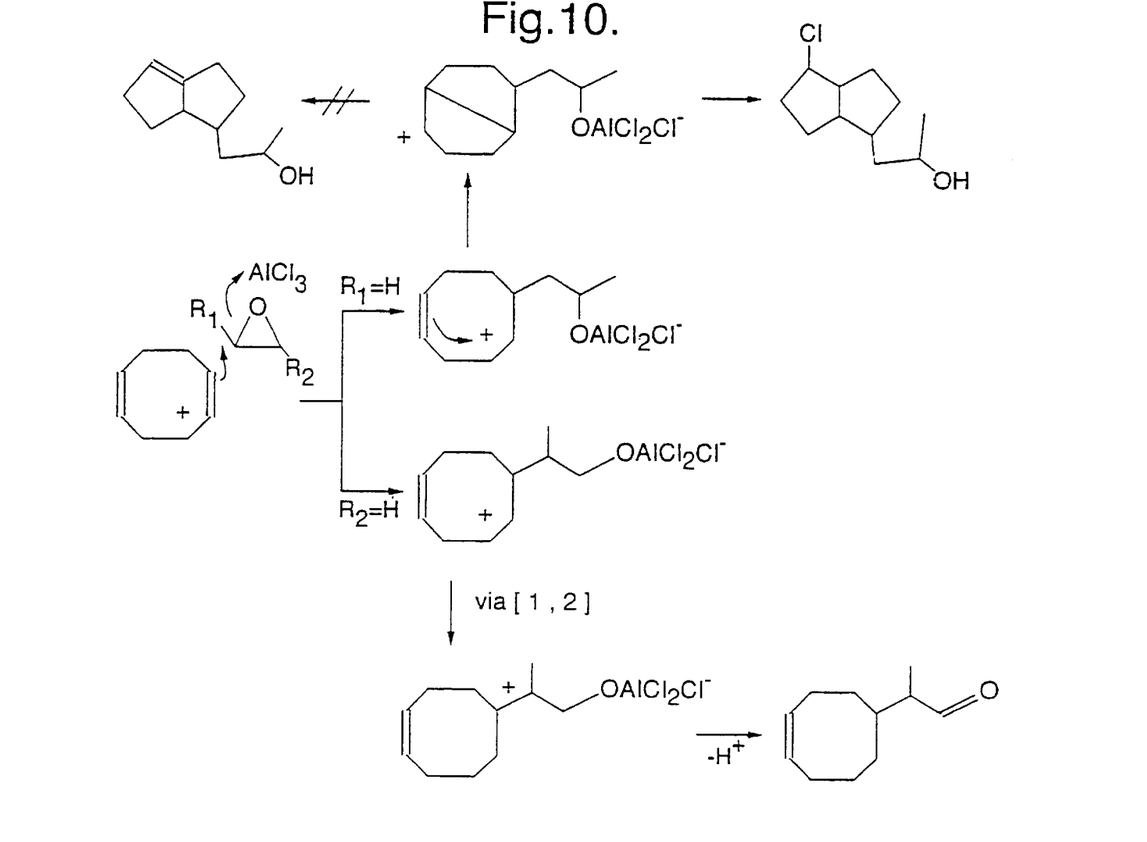
FIG. 10 illustrates further the reaction of FIG. 9.

Again, the presence of the additional double bond enables transannular ring closure as the major reaction pathway, as is illustrated in FIG. 10, here at the expense of the furan products. The strain of the 5,5-fused system makes loss of $H^+$ a less favourable stabilisation pathway, and, in this case, the intermediate carbonium ion is trapped by $Cl^-$ to give QRM 2963, whereas, in the case of 1,5,9-cyclododecatriene, loss of $H^+$ from the intermediate indacene is less disfavoured, and the carbonium ion can also be trapped by the propanol side chain, both with and without skeletal rearrangement, to give the furans (7) and (8) as shown in FIG. 4.

3) Effect of Epoxide Substitution

Another variable in this reaction is the substitution on the epoxide. In order to investigate this, firstly, a series of

TABLE 2

| Cycloalkene | Composition % Cycloalkene | Composition % Product 1 | Composition % Product 2 | % Conversion Product 1 | % Conversion Product 2 |
|---|---|---|---|---|---|
| cyclohexene | 19.80 | 13.73 | 24.45 | 17.10 | 30.50 |
| cyclooctene | 5.05 | 18.71 | 52.34 | 19.70 | 55.10 |
| cyclododecene | 32.92 | 27.31 | 21.34 | 40.70 | 31.80 |

Figure 11:
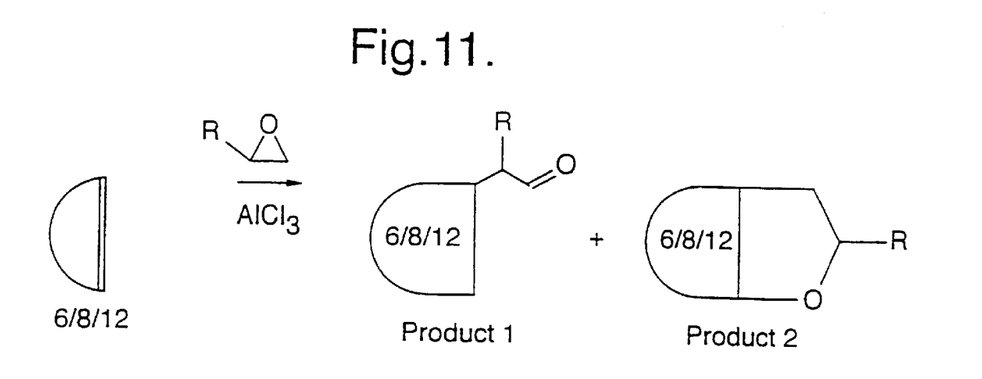
FIG. 11 shows the reaction of cycloalkenes of different ring sizes with mono-substituted epoxides, catalysed by the Lewis acid AlCl$_3$.

These results show cyclooctene to be the most reactive ring system of the three tried. The furan product (Product 2) is also markedly favoured, being produced in almost twice the percentage conversion compared to either the 6- or the 12-membered cycloalkene starting materials.

mono-substituted epoxides was reacted with each of the three cycloalkene ring sizes, previously used. The reaction is illustrated generally in FIG. 11.

The results are summarised in Table 3.

TABLE 3

| cycloalkene | Epoxide substituent R | Composition % cycloalkene | Composition % Product 1 | Composition % Product 2 | % Conversion Product 1 | % Conversion Product 2 |
|---|---|---|---|---|---|---|
| cyclohexene | methyl | 19.80 | 13.73 | 24.45 | 17.10 | 30.50 |
|  | ethyl | 32.52 | 14.61 | 22.75 | 21.70 | 33.70 |
|  | butyl | 21.90 | 11.12 | 19.73 | 14.20 | 25.30 |
| cyclo-octene | methyl | 5.05 | 18.71 | 52.34 | 19.70 | 55.10 |
|  | ethyl | 12.37 | 16.52 | 56.61 | 18.90 | 64.60 |
|  | butyl | 19.76 | 15.52 | 48.14 | 19.30 | 60.00 |
| cyclododecene | methyl | 32.92 | 27.31 | 21.34 | 40.70 | 31.80 |
|  | ethyl | 49.96 | 24.66 | 12.60 | 49.30 | 25.20 |
|  | butyl | 56.16 | 16.51 | 14.16 | 37.70 | 32.30 |

Some general trends can be observed from this data. The larger epoxides tend to lead to a lower percentage consumption of the cycloalkene for each of the ring sizes. Also, the distribution of the products between the aldehyde and the furan seems to be relatively unaffected by the size of the epoxide substituent, unlike the sharp differences influenced by the change in ring size.

Figure 12:
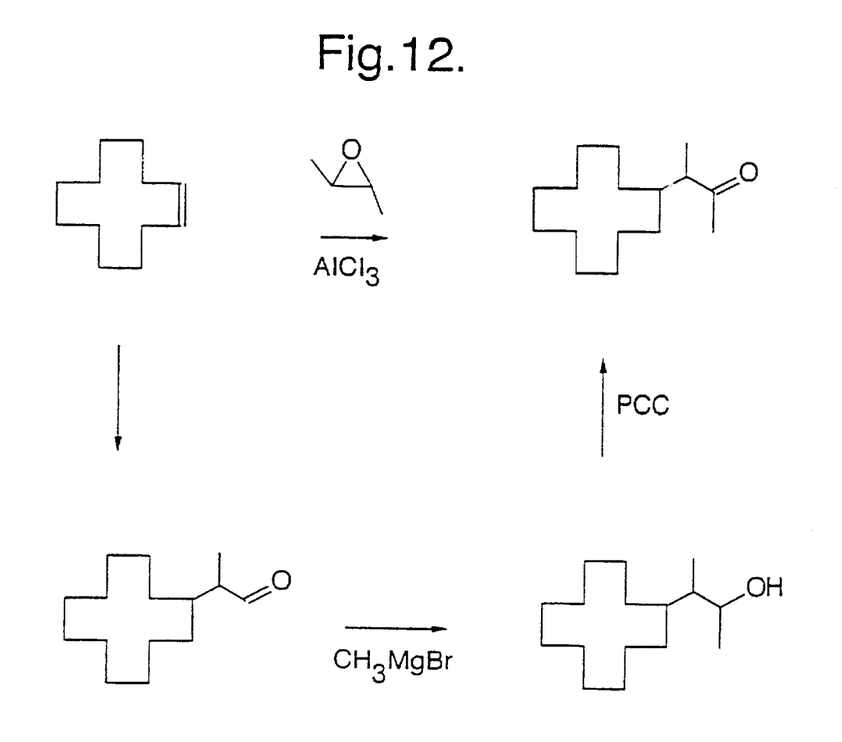
FIG. 12 shows Lewis acid-catalysed reaction of 2,3-epoxybutane with cyclododecene.

Two disubstituted epoxides were also examined. 2,3-Epoxybutane was reacted with cyclododecene in only 14.78% consumption, giving a yield of 8.48% (57.4% conversion), of 3-(cyclododecyl)butan-2one, (referred to herein as QRM 2355). The structure of QRM 2355 was confirmed by comparison with a sample of QRM 2355 prepared via Grignard reaction on QRM 2173. These reactions are illustrated in FIG. 12.

Figure 13:
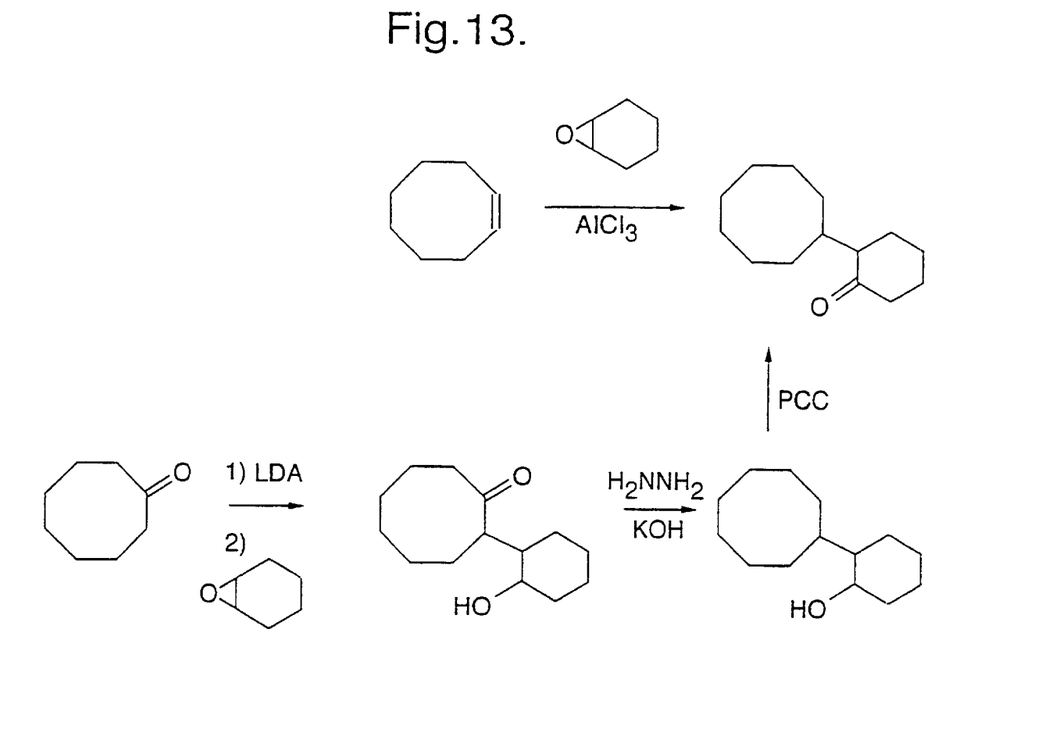
FIG. 13 shows Lewis acid-catalysed reaction of cyclohexene oxide with cyclooctene.

Also, cyclohexene oxide was reacted with cyclooctene and cyclododecene. The reaction with cyclododecene proceeded to less than 10% consumption. However, with cyclooctene, a consumption of 45.35% was observed. The major product was 2-(cyclooctyl)cyclo-hexanone (referred to herein as QRM 2616), which could be compared to a sample of QRM 2616 prepared by an unambiguous route from cyclooctanone. These reactions are illustrated in FIG. 13.

4) Effect of Solvent

Using the original conditions specified in this Example, dichloromethane was replaced by a less polar hydrocarbon solvent, cyclohexane, but almost no reaction was observed. As this was thought to be due to the poor solubility of the intermediate $AlCl_3$-epoxide complex, the much more polar solvent, nitromethane, was also investigated. Here, however, only 10% of the cyclododecene was consumed, and neither the aldehyde nor furan were major products by glc.

EXAMPLE 4

Lewis Acid-Catalysed Reaction of Epoxides with Open-Chain Alkenes

1) Synthesis of Karanal Diol

Figure 14:
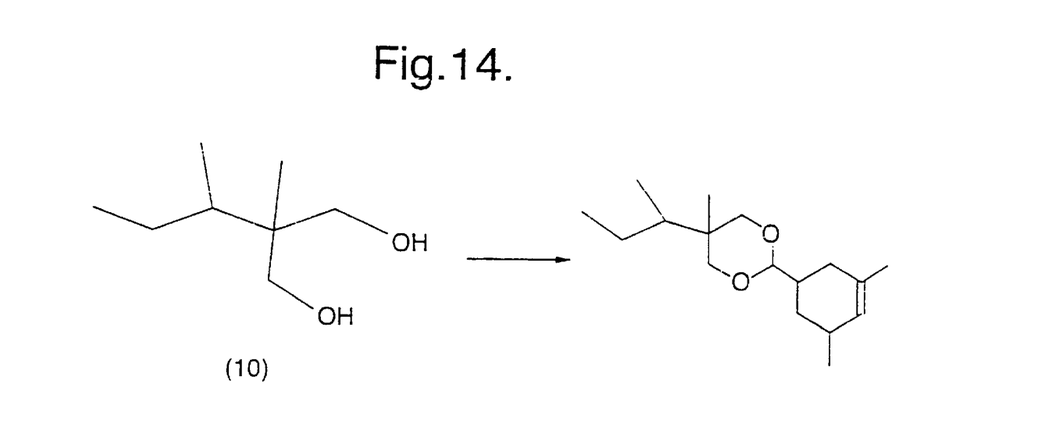
FIG. 14 illustrates production of Karanal from 2-methyl-2-(1-methylpropyl)propane-1,3-diol.
Figure 15:
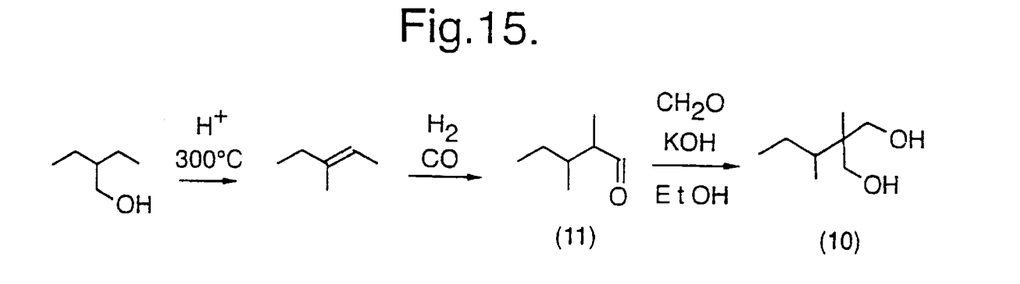
FIG. 15 is a reaction scheme for production of 2-methyl-2-(1-methylpropyl)propane-1,3-diol.

As illustrated in FIG. 14, 2-methyl-2-(1-methylpropyl) propane-1,3-diol (10) is used to make Karanal (Karanal is a Trade Mark of Quest), which is a Quest material having intense amber character, with woody, floral overtones. The diol (10) is currently made by a process involving hydroformylation of 3methylpent-2-ene, followed by Tollen's reaction. as shown in FIG. 15.

Figure 16:
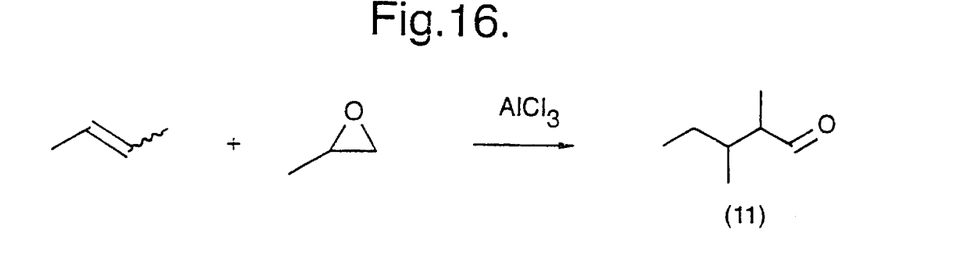
FIG. 16 illustrates Lewis acid-catalysed reaction of but-2-ene with propylene oxide to give 2,3-dimethylpentanal, which can be used for production of 2-methyl-2-(1-methylpropyl)propane-1,3-diol and hence Karanal.

The reaction of the present invention can be used in the production of 2-methyl-2-(1-methylpropyl)propane-1,3-diol (10), by reacting but-2-ene and propylene oxide, using $AlCl_3$ as catalyst, to give 2,3-dimethylpentanal (11) in 33% yield, as shown in FIG. 16. The 2,3-dimethylpentanal can then be reacted to produce 2-methyl-2-(1-methylpropyl)propane-1, 3-diol (10), as shown in FIG. 15, avoiding the need for the dehydration-rearrangement or the hydroformylation of FIG. 15.

2) Reaction of Exo-methylenecycloalkanes

Figure 17:
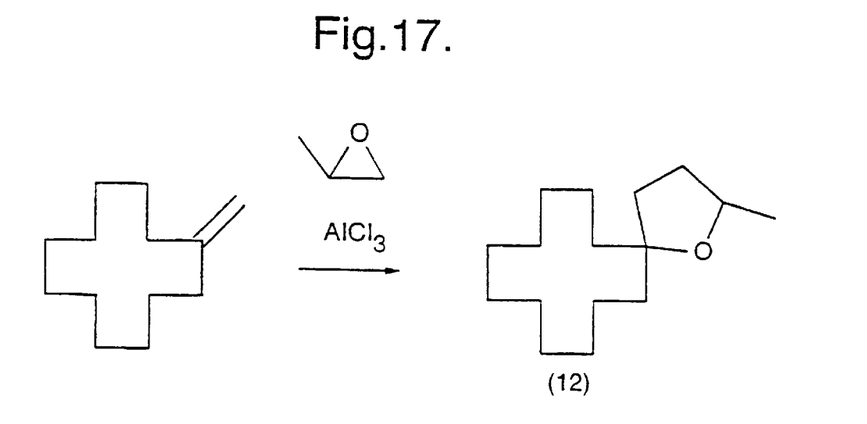
FIG. 17 illustrates Lewis acid-catalysed reaction of exomethylene cyclododecane with propylene oxide.

Exo-methylenecyclododecane has been reacted with propylene oxide to give the oxaspirocycloalkane illustrated in FIG. 17. Related oxaspirocyclooctanes are known to be of fragrance utility. Again, these are usually obtained by multistage procedures.

Exo-methylenecyclododecane (17 g; 0.094 mol) and propylene oxide (9 g; 0.15 mol) were dissolved together in $CH_2Cl_2$ (50 ml), and the solution added dropwise, with stirring, to a suspension of $AlCl_3$ (15 g; 0.112 mol) in $CH_2Cl_2$, maintaining the exothermic reaction between −50° C. and −40° C. The reaction mixture was immediately quenched in ice-water, and extracted into $CH_2Cl_2$. The organic layer was separated, washed, and dried over $MgSO_4$, then the solvent was removed in vacuo. The residue was chromatographed [silica, $CHCl_3$] to give recovered alkene (3.6 g), followed by a colourless oil (9.1 g). Analysis by glc [SE 52: 100–200° C. at 4° C./min] showed 3 products. These appeared to be separable under less polar chromatographic conditions [silica; hexane 50%, $CH_2Cl_2$ 50%]. However, so far, only one of these has been obtained pure, being 5'-methylspiro[cyclododecane1,2'-perhydrofuran] (referred to herein as QRM 2300) (2.2 g), bp 110° C. at 1 mbar.

| $^1$H NMR ($CDCl_3$) | Signal | Multiplicity | Area | Assignment |
|---|---|---|---|---|
| | 4.09 | q | 1 | $OCHCH_3$ |
| | 2.04–1.30 | m | 26 | $CH_2$ |
| | 1.21 | d | 3 | $CH_3$ |

$^{13}$C NMR($\underline{C}DCl_3$), 85.604($\underline{C}(CH_2)_3O$, quaternary), 73.790(O$\underline{C}HCH_3$), 36.629($CH_2$), 34.938($CH_2$), 33.310 ($CH_2$), 33.273($CH_2$), 26.507($CH_2$), 26.461($CH_2$), 26.041 ($CH_2$), 22.383($CH_2$), 22.145($CH_2$), 22.099($CH_3$), 21.871 ($CH_2$), 20.079($CH_2$), 19.804($CH_2$).

What is claimed is:

1. A synthetic method comprising forming an aldehyde by Lewis acid-catalysed reaction of an alkene with an epoxide.

2. A synthetic method according to claim 1, further comprising reducing the aldehyde to the corresponding alcohol.

3. A method according to claim 1, wherein Cyciododecene and propylene oxide are reacted to produce 2-(cyclododecyl)propan-1-al and 2-methylperhydro-cyclododeca[b]furan.

4. A method according to claim 1 wherein the Lewis acid is $SnCl_4$.

5. A method according to claim 3 or 4, wherein the 2-(cyclododecyl)propan-1-al is reduced to 2-(cyclododecyl) propan-1-ol.

6. A method according to claim 1, wherein 1,5,9-cyclododecatriene and propylene oxide are reacted to produce 2-(cyclododecadienyl)1-propanal, 2-methyl-2,3,3a,4,5, 8,9,12,13,13a-decahydrocyclododeca[b]furan and 2-methylperhydro-as-indaceno[3a,3-b]furan.

7. A method according to claim 6, wherein the 2-(cyclododecadienyl)-1-propanal is reduced to 2-(cyclododecadienyl)-1-propanol.

8. A method according to claim 6, wherein the 2-methyl-2,3,3a,4,5,8,9,12,13,13a-decahydrocyclododeca[b]furan is hydrogenated to give 2-methylperhydrocyclodeca[b]furan.

9. Reaction products of claim 1 or 2.

10. A perfume comprising one or more products in accordance with claim 9 in an olfactively effective amount.

11. A perfume according to claim 10, (wherein the product(s) is present in an amount of at least 0.01% by weight.

12. A perfume according to claim 11, wherein the product(s) is present in an amount in the range 0.1 to 80% by weight.

13. A perfumed product comprising one or more products of claim 9.

14. A perfumed product comprising one or more perfumes according to claim 10.

* * * * *